United States Patent [19]
Pastyr

[11] Patent Number: 5,343,048
[45] Date of Patent: Aug. 30, 1994

[54] CONTOUR COLLIMATOR FOR RADIATION THERAPY

[75] Inventor: Otto Pastyr, Liemen, Fed. Rep. of Germany

[73] Assignee: Siemens Aktiengesellschaft, Munich, Fed. Rep. of Germany

[21] Appl. No.: 11,858

[22] Filed: Feb. 1, 1993

[30] Foreign Application Priority Data

Feb. 7, 1992 [DE] Fed. Rep. of Germany ....... 4203610

[51] Int. Cl.$^5$ .................................................. G21K 1/02
[52] U.S. Cl. .................................. 250/505.1; 378/150; 378/152
[58] Field of Search ................ 250/505.1; 378/152, 378/151, 150, 147

[56] References Cited
U.S. PATENT DOCUMENTS

| | | | |
|---|---|---|---|
| 4,739,173 | 4/1988 | Blosser et al. | 250/505.1 |
| 4,754,147 | 6/1988 | Maughan et al. | 250/505.1 |
| 4,794,629 | 12/1988 | Pastyr et al. | 378/152 |
| 5,012,506 | 4/1991 | Span | 378/152 |
| 5,165,106 | 11/1992 | Barthelmes | 250/505.1 |
| 5,166,531 | 11/1992 | Huntzinger | 250/505.1 |

Primary Examiner—Jack I. Berman
Assistant Examiner—James Beyer
Attorney, Agent, or Firm—Lawrence C. Edelman

[57] ABSTRACT

A contour collimator for shaping a radiation beam for radiation therapy has two sets of radiation-impermeable lamellae disposed opposite each other, with each lamella being individually displaceable toward and away from its counterpart lamella in the other set. The sets of lamella are disposed between lateral walls of holder, at least one of which can be loosened and tightened. The lamellae are normally urged against each other by a spring force acting on each lamella. A user-manipulable mechanism is operable for displacing all of the lamellae in both sets away from each other, so that a form conforming to the desired contour can be placed between the lamellae. The mechanism is then moved to permit the spring force to act on each lamella, causing the lamellae to abut the form. The lamellae are then clamped in position.

11 Claims, 6 Drawing Sheets

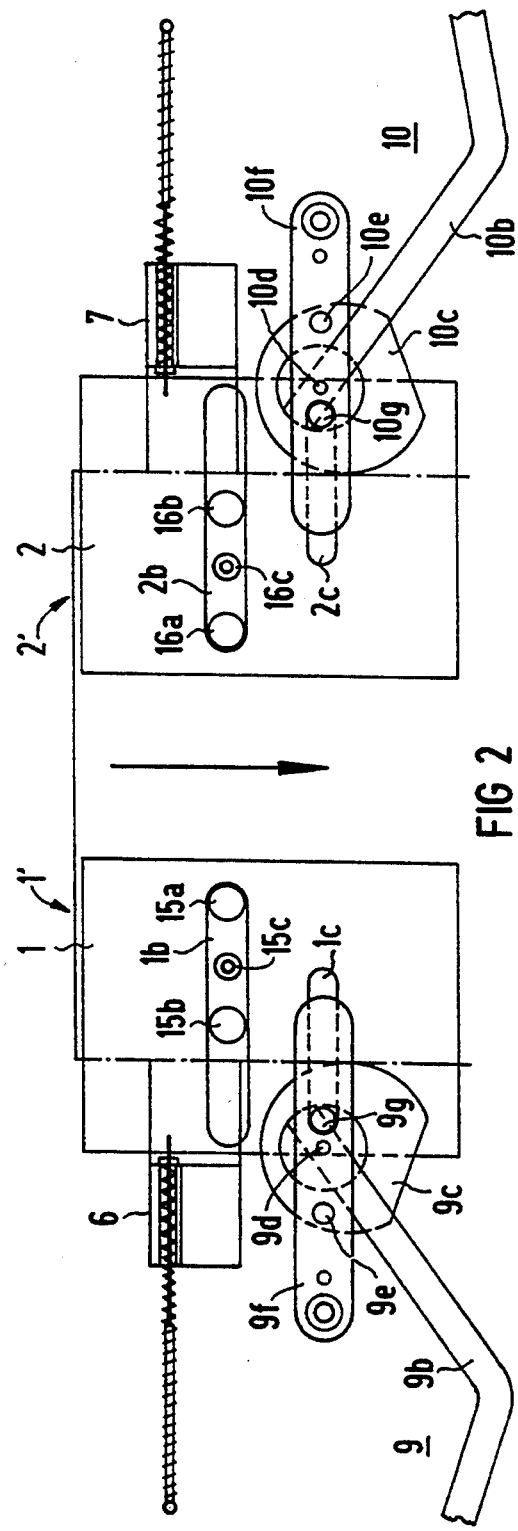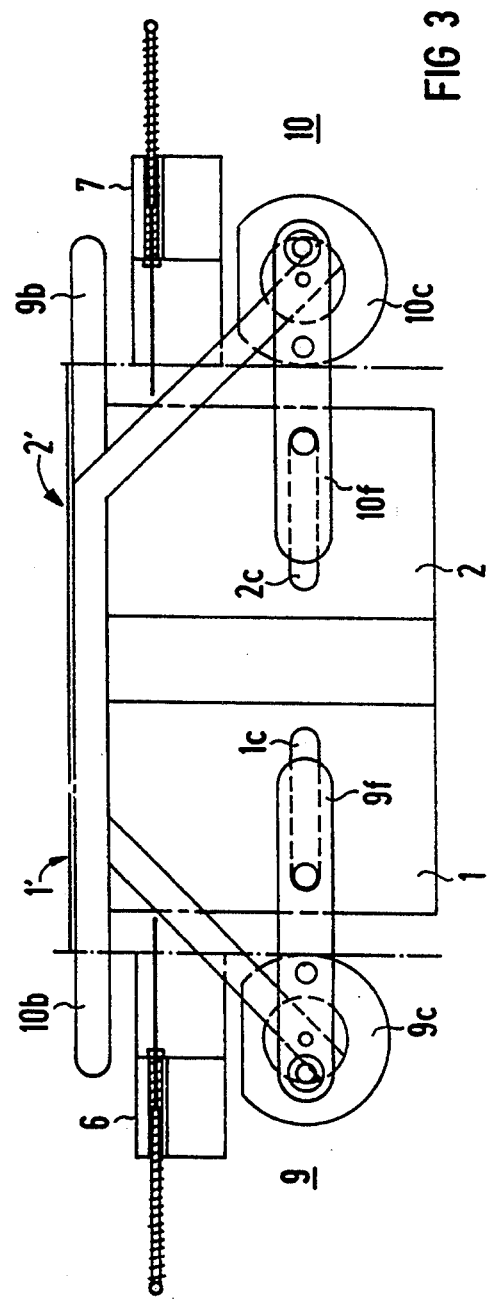

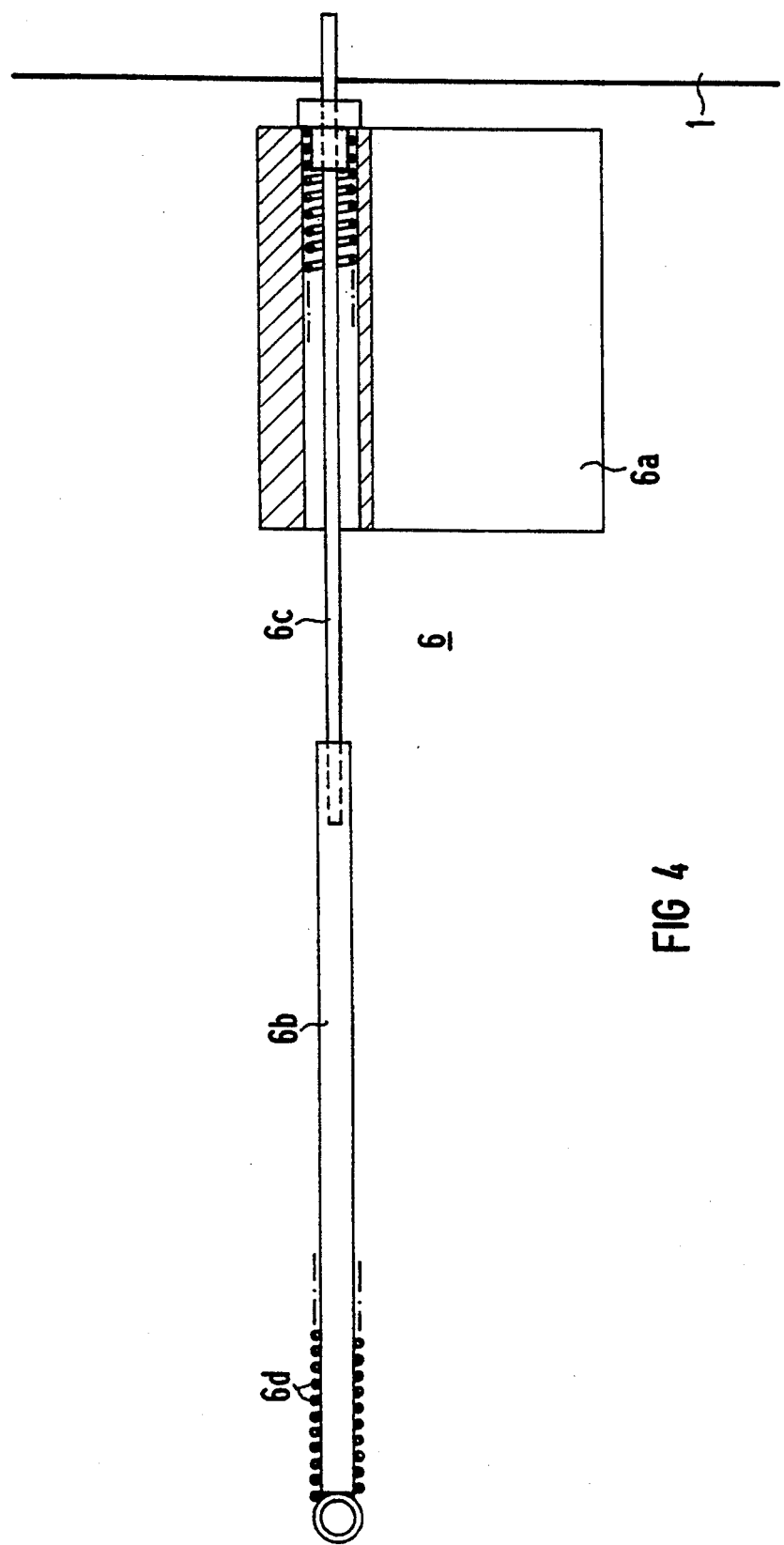

CONTOUR COLLIMATOR FOR RADIATION THERAPY

BACKGROUND OF THE INVENTION

1. Field of the Invention

The present invention is directed to a contour collimator for shaping a radiation beam in radiation therapy, of the type having two sets of individually displaceable lamellae disposed opposite each other, which can be clamped in place in selected positions within a holder.

2. Description of the Prior Art

Contour collimators are utilized for limiting the radiation field of ionizing radiation, such as for oncological radiation therapy, so that the distribution of the radiation dose can be matched to the shape of the target volume, which is usually irregularly shaped, particularly when treating a tumor. A contour collimator is disclosed in European Application 0 387 921 wherein the individual lamellae of two lamellae sets disposed opposite each other can be positioned with a mechanical device so that a radiation field of the desired shape is achieved. In this known apparatus, an adjustment means, for example an electric motor or a user-operable wheel, can be successively coupled to all of the individual lamellae, with the lamellae which are not momentarily coupled to the motor or wheel being locked in place. The shape of the radiation field set by displacing the lamellae can thus be achieved automatically and in a simple manner by actuation of the motor or the wheel. The overall apparatus, however, is relatively complicated and bulky. Moreover, the precision width which a desired shape can be achieved is limited by the thickness of the individual lamellae, with a finer adjustment of the contour being possible with thinner lamellae. In this known apparatus, as the lamellae become increasingly thinner, it is more difficult to couple only one lamella at a time to the displacement mechanism. This known apparatus, therefore, is primarily suitable for larger collimators.

Collimators are also known which are exclusively manually operable, which also include oppositely disposed sets of individually displaceable lamellae. A form matched to the desired radiation field, such as form matched to the shape of a tumor to be treated, is first produced, and is placed into the contour collimator between the sets of lamellae, with the lamellae completely retracted from the path of the radiation beam. The lamellae are then manually pushed against the form and fixed in place. This procedure, however, is time consuming, and it must be assured that all lamellae are positively made to abut the form, in order to avoid harmful irradiation of tissue surrounding tumor. Moreover, given extremely thin lamellae, there is the risk of the operator being cut when manually displacing the lamellae.

A contour collimator is disclosed in U.S. Pat. No. 4,754,147 for radiation therapy having individually displaceable rods disposed opposite each other. Adjustment of the individual rods takes place with the use of form elements at the rod ends, with the collimator being turned so that the individual rods fall against the form due to the force of gravity. The rods are then clamped in place. Adjustment of collimator elements using the force of gravity, however, creates problems because jamming can occur, particularly given lightweight collimator elements. Moreover, the necessary rotation of the collimator requires complicated mechanical devices, and manipulation of the collimator thus also becomes complicated.

SUMMARY OF THE INVENTION

It is an object of the present invention to provide a contour collimator of the type having two sets of individually displaceable lamellae, wherein the lamellae can be displaced to set a desired radiation field contour which has a simple structure and which permits precise placement of the lamellae against a form conforming to the desired radiation field contour.

The above object is achieved in a contour collimator having a holder in which two sets of radiation-impermeable lamellae, each lamella being individually movable toward and away from its counterpart lamella in the other set. The lamellae in both sets are normally urged toward each other by a spring force applied individually to each lamella. Each lamella has a slot, and each slot has a pin engaged therein. The pins are mounted on a means operable by user for collectively displacing the sets of lamellae away from each other against the spring force.

For setting a desired contour the lamellae are moved away from each other and a form conforming to the desired contour is placed between the sets of lamellae. The displacement means is then released by the user, and, under the influence of the spring force, all of the individual lamellae are urged toward the form, so as to abut the form. The sets of lamellae are disposed in the holder between two lateral holder walls, at least one of which is able to be tightened and loosened against each set of lamellae. When the lamellae have been displaced to the desired position by the spring force, the wall is clamped to fix the lamellae in place. The form can then be removed or, if it is sufficiently radiation permeable, can be left in place for conducting the therapy.

DESCRIPTION OF THE DRAWINGS

FIG. 2 is a schematic side elevational view of a contour collimator constructed in accordance with the principles of the present invention with the lamellae in an open position.

FIG. 3 is a schematic side elevational view of a contour collimator constructed in accordance with the principles of the present invention with the lamellae in a closed position.

FIG. 4 is a schematic illustration showing the structure of a spring device for use in the contour collimator of FIGS. 2 and 3.

DESCRIPTION OF THE PREFERRED EMBODIMENTS

Figure 1:
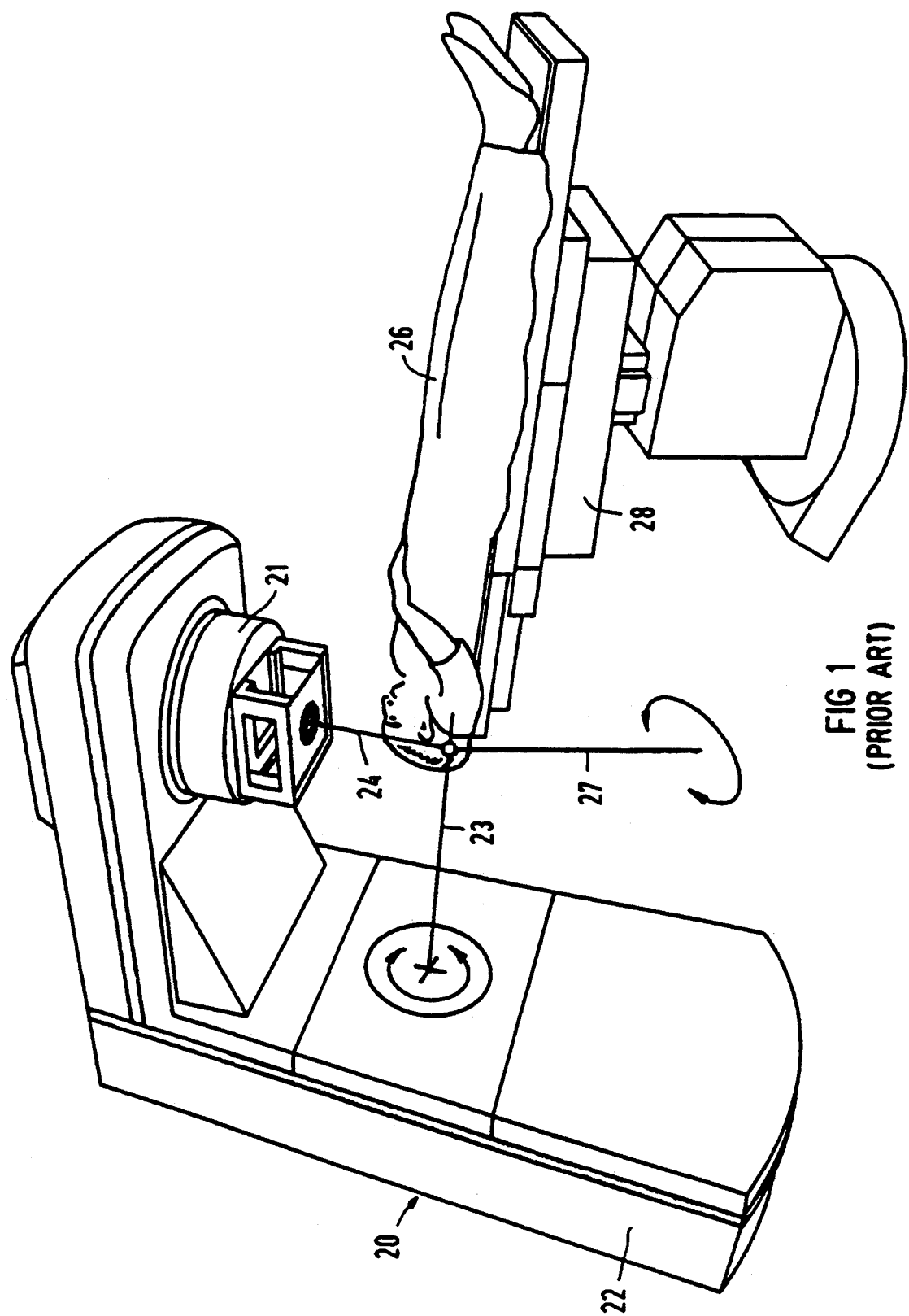
FIG. 1 shows a known linear accelerator suitable for radiation therapy, in which a contour collimator constructed in accordance with the principles of the present invention can be utilized.

A linear accelerator 20 of a known type is shown in FIG. 1, in which a contour collimator 21 constructed in accordance with the principles of the present invention can be utilized. The linear accelerator 20 has a gantry 22 which contains the contour collimator 21, the gantry 22 being rotatable around a horizontal axis 23 during the course of a therapeutic treatment. The center of the radiation beam which is incident on a patient 26 from the linear accelerator 20 is referenced 24. The patient 26 is disposed during treatment on a table 28, which is positionable in a known manner in coordination with the positioning of the radiation beam so that intersection of the center axis 24 of the radiation beam with a desired isocenter is maintained during the treatment. The table 28 is rotatable around an axis 27, which intersects the isocenter for this purpose.

An exemplary embodiment of a contour collimator 21 constructed in accordance with the principles of the present invention is shown in FIGS. 2, 3, 5 and 6, with individual details being shown in the other figures.

FIG. 2 shows the two lamella sets 1' and 2' in an open position in a side view. The lamella sets each consist of a plurality of lamellae disposed parallel to the plane of the drawing in FIG. 2, so that only the respective end lamellae 1 and 2 of each set 1, and 2' can be seen. Each lamella is radiation impermeable, and functions as a diaphragm plate for blanking the radiation from the linear accelerator, which is incident in the direction indicated with an arrow in FIG. 2. Further structure will be described with respect to the end lamellae 1 and 2, however, it will be understood that, unless otherwise indicated, identical structure exists for each of the other lamellae.

The individual lamellae 1 and 2 are urged to the closed position shown in FIG. 3 by respective spring devices 6 and 7. The lamella 1 has a guide slot 1b and the lamella 2 has a guide slot 2b. Two guide pins 15a and 15b are engaged in the slot 1b, and two guide pins 16a and 16b are received in the guide slot 2b. The guide pins 15a and 15b and 16a and 16b extend the width of the collimator and engage the guide slots for all lamellae in the set through which they respectively extend. Additionally, a spring pin 15c also extends through guide slot 1b in each lamella in the lamella set 1' and a spring pin 16c extends through each guide slot 2b in all of the lamellae in the set 2'. The spring pins 15c and 16c respectively force the lateral walls 3 and 4 (described below in connection with FIG. 5) away from the lamellae in order to enable smooth gliding of the lamellae 1 and 2.

As shown in FIG. 2, the two lamellae sets 1', 2' are held in an open position by respectively displacement mechanisms 9 and 10, against the spring force exerted by the spring devices 6 and 7. The displacement mechanisms 9 and 10 respectively include cams 9c and 10c which are respectively rotated by handles 9b and 10b. The cam 9c has a lever 9f secured thereto at a pivot point 9e and the cam 10c has a lever 10f secured thereto at a pivot point 10e. Each lamella in the set 1' has a further slot 1c therein, and each lamella in the set 2' has a further slot 2c therein. The lever 9f has a pin or rod 9g which extends through each slot 1c in each lamella in the set 1', and the lever 10f has a pin or rod 10g which extends through the slot 2c in each of the lamella in the set 2'.

When the handles 9b and 10b are manipulated to respective positions toward the outside of the collimator, the pins 9g and 10g pull the lamellae in the sets 1' and 2' away from each other against the force of the spring devices 6 and 7.

When the handles 9b and 10b are moved toward the inside of the collimator, as shown in FIG. 3, the lamellae in the sets 1' and 2' are collectively moved toward each other by the forces exerted by the respective spring devices 6 and 7. If no object is placed between the lamellae in the sets 1' and 2', the collimator will be completely closed, i.e., the lamellae such as the lamellae 1 and 2 will abut each other. As indicated by the dashed lines in FIG. 3, however, the range of movement of each lamella, such as the lamellae 1 and 2, extends beyond a center line between the lamellae in order, for example, to achieve a kidney-shaped contour which intersects the center line. It will be understood, however, that counterpart lamellae such as the lamellae 1 and 2, could not simultaneously be extended to their extreme positions.

If an object is inserted between the lamellae in the sets 1' and 2', the lamellae will position themselves against the outer contour of the object. For radiation therapy, an object, for example a wooden form matched to the desired radiation profile, is placed between the lamella in the sets 1' and 2' with the handles 9b and 10b in the open position shown in FIG. 2. The handles 9b and 10b are then brought to the closed position shown in FIG. 3, so that the lamellae are urged by the spring devices 6 and 7 against the form. The guide slots 1b and 2b are omitted in FIG. 3 for clarity.

A spring device 6 for an individual lamella is shown enlarged in FIG. 4. The spring device 7 of FIG. 2 is identically constructed, and is therefore does not separately illustrated. Each spring device 6 is composed of a retainer block 6a, a piston 6b, a thrust rod 6c and a spring 6d. The thrust rod 6c is rigidly attached to an associated lamella, such as the lamella 1. The retainer block 6a is rigidly mounted on a carrier of the contour collimator, the carrier being omitted in the drawing for clarity. The spring 6d is a tension spring, and thus presses the lamella 1 away from the retainer block 6a. The piston 6b serves the purpose of guiding the spring 6d.

Figure 5:
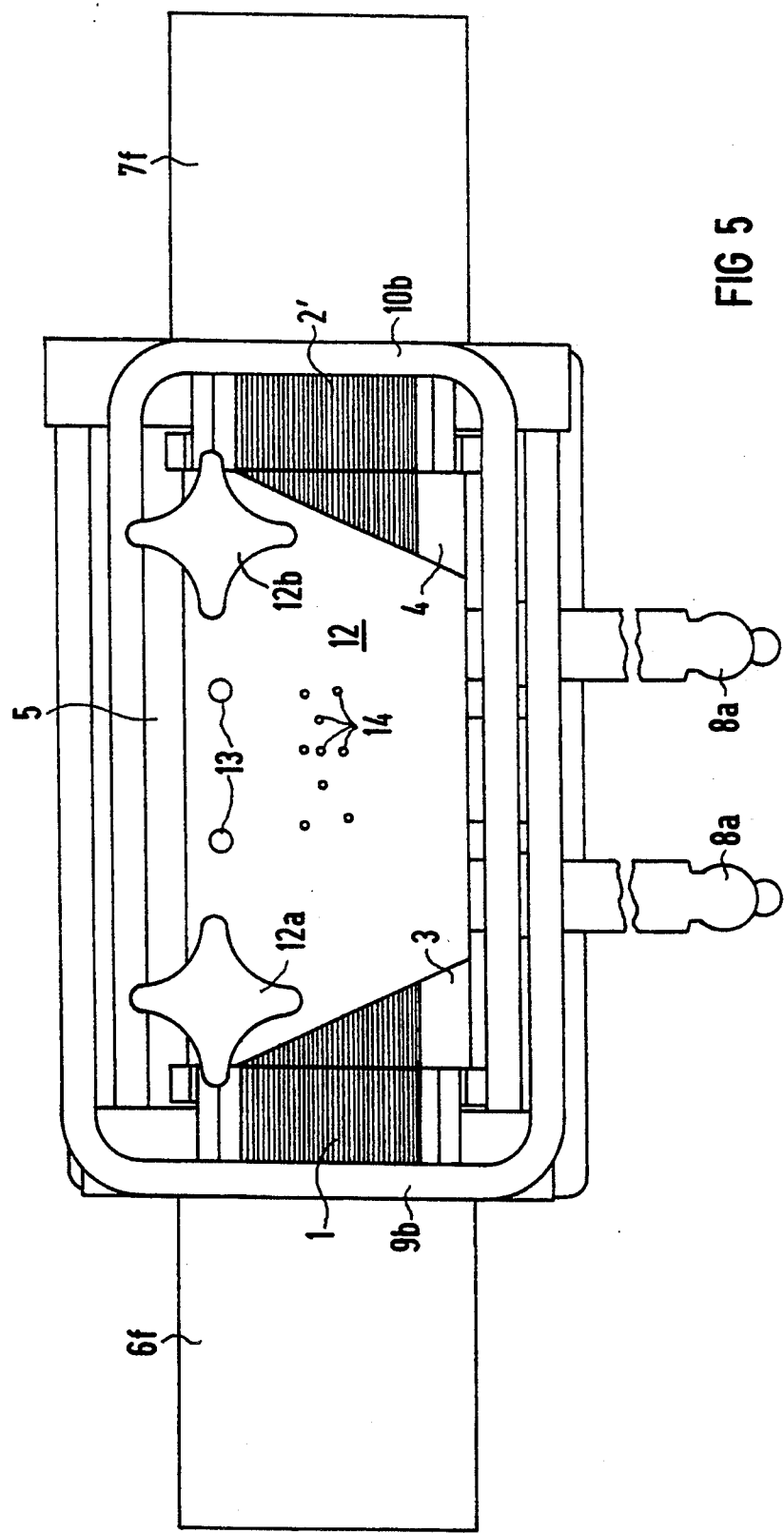
FIG. 5 is a plan view of the collimator constructed in accordance with the principles of the present invention.

A plan view of the beam collimator is shown in FIG. 5. Housings 6f and 7f containing the spring devices 6 and 7 can be seen at both sides. A form-holding plate 12 is removably secured to the beam collimator by two knobbed screws 12a and 12b. The form which defines the radiation profile is introduced between the lamellae sets 1' and 2' by means of the form-holding plate 12. In order to be able to exactly spatially position the form-holding plate 12 with respect to the contour collimator, two index pins 13 are attached to the form-holding plate 12. Further, positioning pins 14 are provided at the form-holding plate 12 in order to assure exact positioning of the form to be inserted. These positioning pins 14 are arranged so that a skewed introduction of the form is not possible, and such that forms which are asymmetrical with respect to the center line can also be exactly positioned.

During irradiation, the individual lamellae, such as the lamellae 1 and 2, are secured in their respective positions prescribed by the inserted form by being clamped together by the operation of clamp toggles 8a. The guide pins 15a and 16a, shown in FIG. 2 are held by the lateral walls 3 and 4, and each have a threaded end received in the respective clamp toggles 8a. When the clamp toggles 8a are turned, the lamellae in the sets 1 and 2 are pressed together, and are thus fixed in their positions. Independently of this clamping, however, the inserted form can remain in position during irradiation, if it has a sufficiently low radiation absorption (such as the form consists, for example, of wood).

Figure 6:
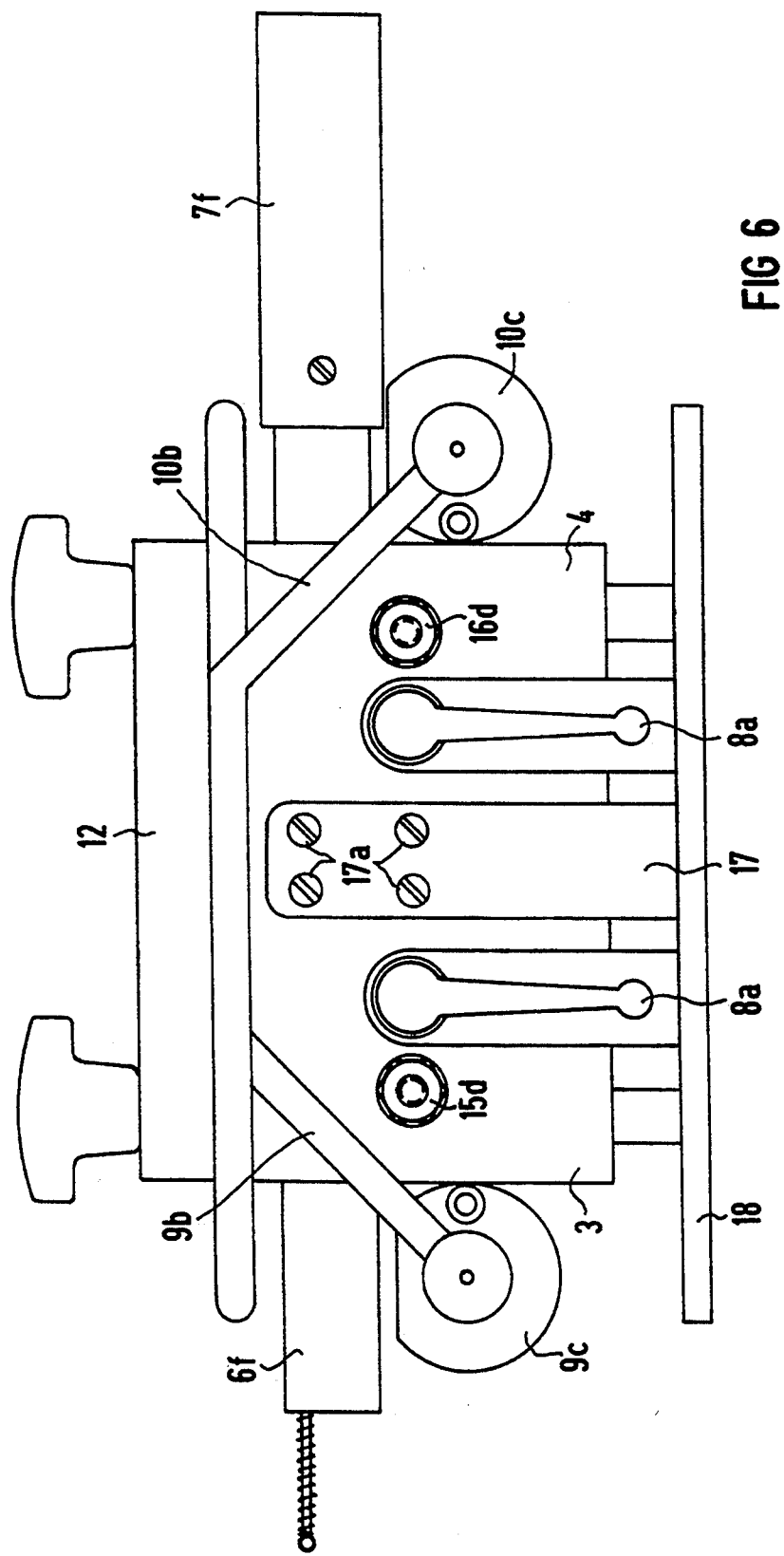
FIG. 6 is a front view of the contour collimator constructed in accordance with the principles of the present invention.

A front view of the contour collimator is shown in FIG. 6. The two clamp toggles 8a can be clearly seen. As can also be seen in FIG. 6, the two lateral walls 3 and 4 are separated, so that the lamella sets 1' and 2' can be separately fixed in position. The form-holding plate 12, the handles 9b and 10b, the cams 9c and 10c and housings 6f and 7f for the spring devices 6 and 7 can also be again seen in FIG. 6. The guide pins 15b and 16b are secured by respective fasteners 15d and 16d.

A support 17, having four contact springs 17a, is mounted to a base plate 18. The contact spring 17a press against the lateral walls 3 and 4 so that the inside edges of the lateral walls 3 and 4 are forced slightly together, and thus also press the exterior sides of the lamellae 1 and 2 slightly together. This prevents the lamellae 1 and 2 from sliding along a contour which is substantially parallel to the lamellae 1 and 2 when the collimator is closed and then being clamped in such a position. In their non-clamped condition, the lateral walls 3 and 4 extend slightly wedge-shaped, i.e., because the inside surfaces of the lateral walls 3 and 4 are pressed together by the contact springs 17a, and are simultaneously forced apart by the spring pins 15c and 16c shown in FIG. 2.

Figure 7:
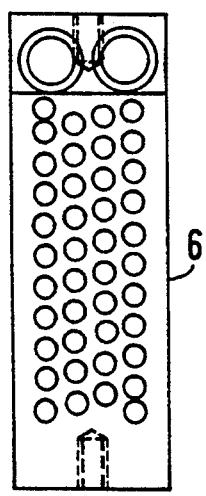
FIG. 7 is a view of a plurality of spring devices as shown in FIG. 4, as "seen" by a set of lamellae.

A view of the plurality of spring devices which respectively act on the lamellae sets 1' and 2' is shown in FIG. 7 as "seen" by the set. As can be seen in FIG. 7, the individual spring devices are offset relative to each other, in order to obtain the small spacing between the spring devices necessitated by the thinness of the lamellae.

Although modifications and changes may be suggested by those skilled in the art, it is the intention of the inventor to embody within the patent warranted hereon all changes and modifications as reasonably and properly come within the scope of his contribution to the art.

I claim as my invention:

1. A contour collimator for shaping a radiation beam comprising:
   a holder;
   two sets of radiation-impermeable lamellae disposed in said holder, each lamella in each set being individually movable toward and away from a corresponding lamella in the other set;
   each lamella having a displacement element engager;
   two spring means, coupled to and respectively acting on said two sets of lamellae, for generating a spring force for normally urging all lamellae in a set toward the lamellae in the other set;
   two displacement elements respectively engaging said displacement element engagers of said lamellae in said sets of lamellae; and
   two user-manipulable means, on which said displacement elements are respectively mounted, operable in a first manner for moving said displacement elements so as to collectively displace said sets of lamellae away from each other against said spring force and operable in a second manner for releasing said sets of lamellae so as to permit said spring force to act thereon and urge all lamella in a set toward the lamella in the other set.

2. A contour collimator as claimed in claim 1 wherein each spring means comprises a plurality of springs corresponding in number and uniquely allocated to the lamellae in a respective one of said two sets of lamellae.

3. A contour collimator as claimed in claim 2 wherein said spring means comprises a plurality of thrust rods respectively interacting with each spring and the lamella allocated thereto, each spring forcing a thrust rod against its allocated lamella.

4. A contour collimator as claimed in claim 1 further comprising means for clamping said lamellae in said sets of lamellae in a selected position upon said lamellae being released by said user-manipulable means.

5. A contour collimator as claimed in claim 4 wherein said means for clamping comprises movable lateral walls of said holder, and means for moving said movable lateral walls toward and away from said lamellae in said sets.

6. A contour collimator as claimed in claim 5 wherein said movable lateral walls are movable independently of each other.

7. A contour collimator as claimed in claim 1 wherein each lamella has a slot forming said displacement element engager, and wherein each displacement element consists of a pin extending through the respective slots of all lamellae in a set.

8. A contour collimator as claimed in claim 7 wherein each user-manipulable means includes a lever, on which said pin is mounted, and a rotatable cam interacting with said lever to move said pin to displace and to release said lamellae.

9. A contour collimator as claimed in claim 1 further comprising a form-holding plate including means for securing a form between said two sets of lamellae.

10. A contour collimator as claimed in claim 9 wherein said form-holding plate includes index means for defining alignment of said form-holding plate relative to said holder.

11. A contour collimator as claimed in claim 9 wherein said form-holding plate includes positioning means for defining alignment of a form, when secured in said means for securing, relative to said holder.

* * * * *